US008963554B2

(12) United States Patent
Stearns et al.

(10) Patent No.: US 8,963,554 B2
(45) Date of Patent: Feb. 24, 2015

(54) PULSED DISCHARGE HELIUM IONIZATION DETECTOR WITH MULTIPLE COMBINED BIAS/COLLECTING ELECTRODES FOR GAS CHROMATOGRAPHY AND METHOD OF USE

(75) Inventors: Stanley D. Stearns, Houston, TX (US); Huamin Cai, Houston, TX (US)

(73) Assignee: Valco Instruments Company, L.P., Houston, TX (US)

( * ) Notice: Subject to any disclaimer, the term of this patent is extended or adjusted under 35 U.S.C. 154(b) by 414 days.

(21) Appl. No.: 13/592,489

(22) Filed: Aug. 23, 2012

(65) Prior Publication Data

US 2014/0053627 A1  Feb. 27, 2014

(51) Int. Cl.
*G01N 27/62* (2006.01)

(52) U.S. Cl.
USPC ..... 324/464; 324/468; 324/76.67; 324/76.76; 324/122; 324/123 R

(58) Field of Classification Search
USPC ......... 324/409, 410, 411, 412, 414, 468, 464, 324/76.67, 76.76, 122, 123 R, 465
See application file for complete search history.

(56) References Cited

U.S. PATENT DOCUMENTS

| 4,077,773 | A | 3/1978 | Stearns |
|---|---|---|---|
| 5,153,519 | A | 10/1992 | Wentworth et al. |
| 5,317,271 | A | 5/1994 | Wentworth et al. |
| 5,394,090 | A | 2/1995 | Wentworth et al. |
| 5,394,091 | A | 2/1995 | Wentworth et al. |
| 5,394,092 | A | 2/1995 | Wentworth et al. |
| 5,528,150 | A | 6/1996 | Stearns et al. |
| 5,532,599 | A | 7/1996 | Stearns et al. |
| 5,541,519 | A | 7/1996 | Stearns et al. |
| 5,594,346 | A | 1/1997 | Stearns et al. |
| 5,767,683 | A | 6/1998 | Stearns et al. |
| 6,133,740 | A | 10/2000 | Wentworth et al. |
| 6,333,632 | B1 | 12/2001 | Yang et al. |
| 6,448,777 | B1 * | 9/2002 | Abdel-Rahman et al. .... 324/464 |
| 6,842,008 | B2 | 1/2005 | Stearns et al. |
| 2004/0118348 | A1 | 6/2004 | Mills |
| 2004/0245993 | A1 * | 12/2004 | Bonne .......................... 324/464 |
| 2008/0048663 | A1 * | 2/2008 | Hong et al. ................... 324/464 |
| 2008/0188013 | A1 | 8/2008 | Cho et al. |

OTHER PUBLICATIONS

Brian Sircus, Notification of Transmittal of International Preliminary Report on Patentability—PCT/US13/56394, Jul. 22, 2014, 1 page, United States Patent & Trademark Office as International Search Authority, Alexandria, Virginia USA.
Brian Sircus, International Preliminary Report on Patentability—PCT/US13/56394, Jul. 21, 2014, 8 pages, United States Patent & Trademark Office as International Search Authority, Alexandria, Virginia USA.
VICI Valco Instruments Co., Inc, Pulsed Discharge Detector Models D-2 and D-2-1 Instruction Manual PDD. p65, Jul. 2009, 32 pages, VICI Valco Instruments Co., Inc., United States of America.

(Continued)

*Primary Examiner* — Huy Q Phan
*Assistant Examiner* — Temilade S Rhodes-Vivour
(74) *Attorney, Agent, or Firm* — Crain, Caton & James, P.C.; James E. Hudson, III

(57) ABSTRACT

A pulsed discharge helium ionization detector for gas chromatography with multiple combined bias/collecting electrodes.

14 Claims, 6 Drawing Sheets

(56) References Cited

OTHER PUBLICATIONS

Lee W. Young, Notification of Transmittal of the International Search Report and the Written Opinion of the International Searching Authority, or the Declaration—PCT/US13/56394, Feb. 3, 2014, 1 page, US Patent & Trademark Office as International Searching Authority, Alexandria, Virginia, United States of America.

Lee W. Young, International Search Report—PCT/US13/56394, Feb. 3, 2014, 2 pages, US Patent & Trademark Office as International Searching Authority, Alexandria, Virginia, United States of America.

Lee W. Young, Written Opinion of the International Searching Authority—PCT/US13/56394, Jan. 12, 2014, 6 pages, US Patent & Trademark Office as International Searching Authority, Alexandria, Virginia, United States of America.

* cited by examiner

US 8,963,554 B2

PULSED DISCHARGE HELIUM IONIZATION DETECTOR WITH MULTIPLE COMBINED BIAS/COLLECTING ELECTRODES FOR GAS CHROMATOGRAPHY AND METHOD OF USE

CROSS-REFERENCE TO RELATED APPLICATIONS

None.

STATEMENT REGARDING FEDERALLY SPONSORED RESEARCH OR DEVELOPMENT

Not Applicable.

BACKGROUND OF THE INVENTION

1. Field of Invention

The present invention pertains to pulsed discharge helium ionization detectors for gas chromatography and methods of use. More specifically, the present invention relates to a pulsed discharge helium ionization detector for gas chromatography with multiple combined bias/collecting electrodes and to methods of use.

2. Description of the Related Art

Gas chromatograph systems used to detect the presence of specific compounds include the well-known use of ionization detectors. Sample gas, separated according to boiling point in a gas column, is flowed into an ionization detector where it undergoes an ionization process. The separated constituents become ionized according to their composition, which is detected and measured by a collecting electrode within the ionization detector.

Variations of the gas discharge detector exist, including those which use a direct current discharge or an alternating current discharge and others which use a dielectric barrier discharge. The original gas detector and the variations share a common construction—the use of a single collecting electrode. Unfortunately, use of a single bias/collecting electrode limits the information which may be obtained from within the detector cell.

Thus, there is a need in the art for a pulsed discharge helium ionization detector for gas chromatography with multiple combined bias/collecting electrodes. A pulsed discharge helium ionization detector with multiple combined bias/collecting electrodes would provide better performance, including higher sensitivity, larger linear range, faster response, lower gas consumption, and limited qualification capability.

SUMMARY OF THE INVENTION

The present invention therefore meets the above needs and overcomes one or more deficiencies in the prior art by providing a pulsed discharge helium ionization detector for gas chromatography with multiple combined bias/collecting electrodes.

The invention includes a detector body 108 having an internal ionization source and a plurality of voltage-biased bias/collecting electrodes, a current-to-voltage converter associated with each voltage-biased bias/collecting electrode, at least one voltage polarity inverter, at least one gain adjuster, and a time-dependent voltage aggregator, by which multiple detections of electrode collection of current is converted to a voltage domain, are adjusted to provide a common intensity based on detector body geometry, are adjusted to account for delay time in detection based on detector body geometry, and are averaged to provide a time dependent average output to determination of constituent compounds in the eluted sample, which may be stored or displayed as a chromatogram.

The multiple combined bias/collecting electrode pulsed discharge helium ionization detector can efficiently correct peak distortion caused by uneven photon intensity in a cylindrical detector cell. It also offers the advantages of high sensitivity and a large linear range compared with the typical, and single-collecting, PDHID.

Additional aspects, advantages, and embodiments of the invention will become apparent to those skilled in the art from the following description of the various embodiments and related drawings.

BRIEF DESCRIPTION OF THE DRAWINGS

So that the manner in which the described features, advantages, and objects of the invention, as well as others which will become apparent, are attained and can be understood in detail; more particular description of the invention briefly summarized above may be had by referring to the embodiments thereof that are illustrated in the drawings, which drawings form a part of this specification. It is to be noted, however, that the appended drawings illustrate only typical preferred embodiments of the invention and are therefore not to be considered limiting of its scope as the invention may admit to other equally effective embodiments.

In the drawings.

DESCRIPTION OF THE PREFERRED EMBODIMENT

Figure 2:
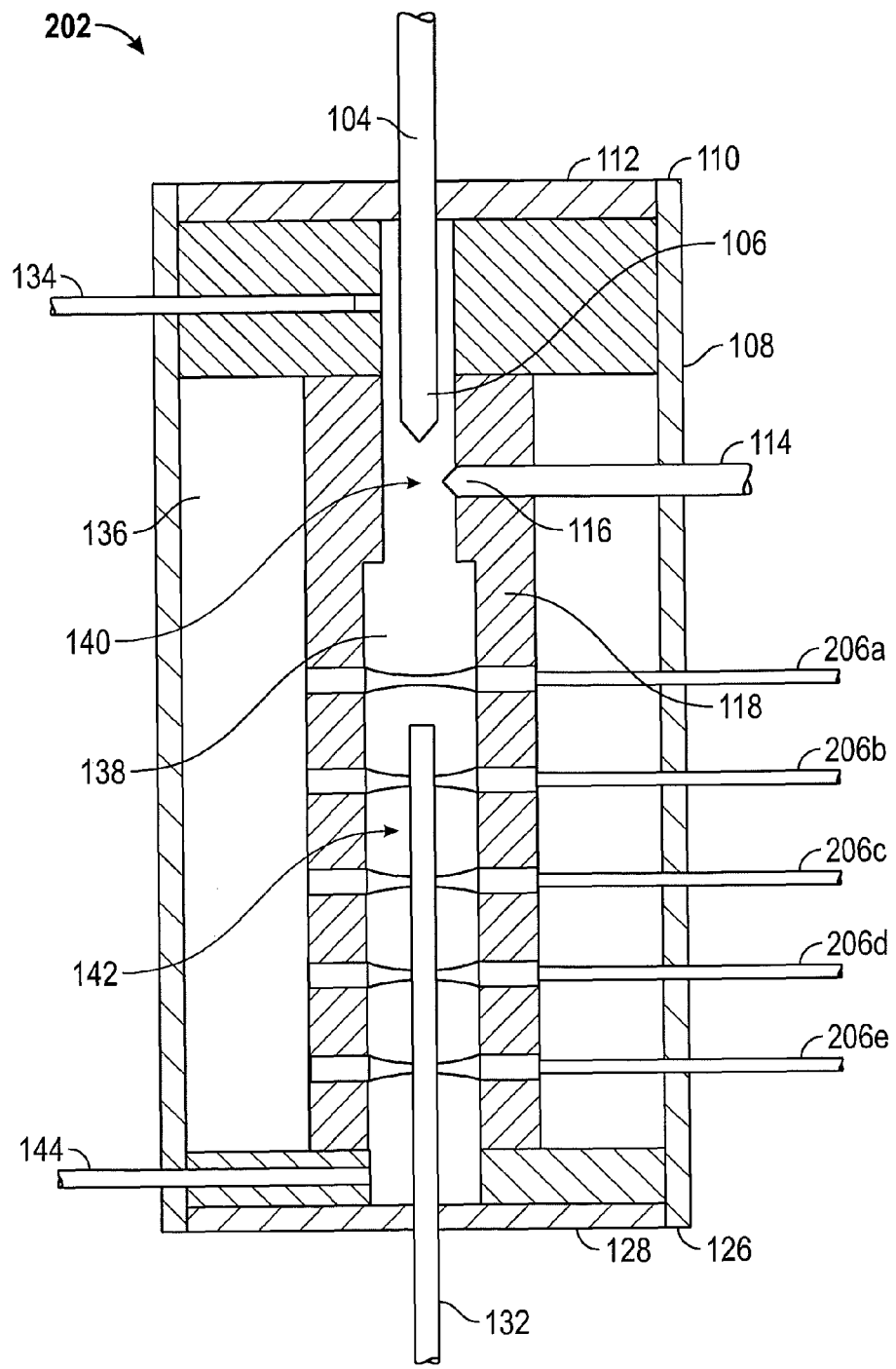
FIG. 2 is an illustration of a pulsed-discharge detector the present invention.
Figure 3:
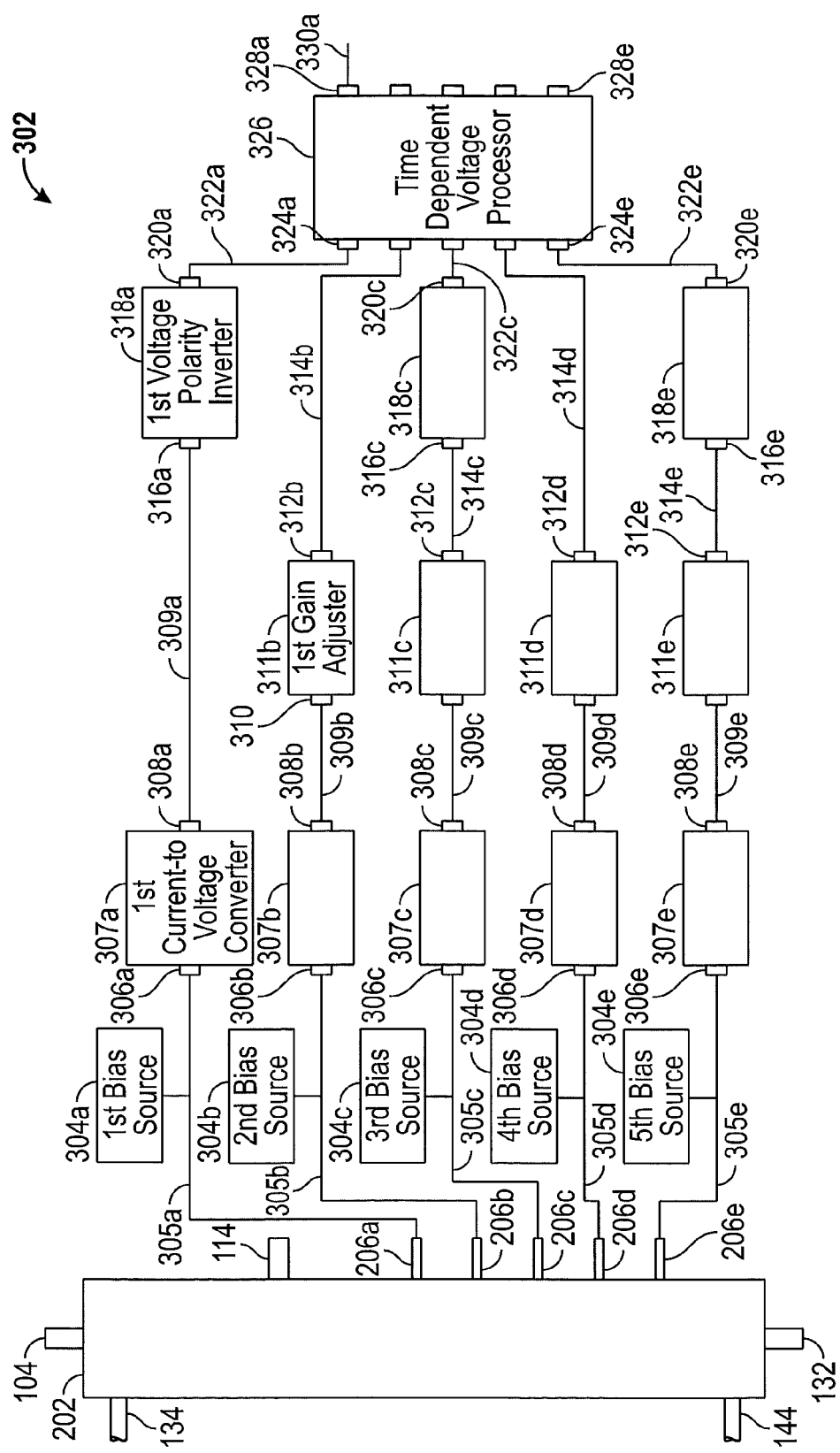
FIG. 3 is an illustration of a pulsed-discharge detector system using the disclosed pulsed-discharge detector.

Referring to FIGS. 2 and 3, the invention provides a pulsed discharge helium ionization detector 202 for gas chromatography with multiple combined bias/collecting electrodes and to methods of use.

The detector system 302 includes a detector body 108, a plurality of bias sources 304a, 304b, 304c, 304d, 304e, an equal plurality of current-to-voltage converters 307a, 307b, 307c, 307d, 307e, a gain adjuster 311b, 311c, 311d, 311e associated with all but one current-to-voltage converters 307b, 307c, 307d, 307e, at least one voltage polarity inverter 318b, 318d, and a time-dependent voltage processor 326. The detector body 108 has an internal and open cylindrical cell 138, having a centerline 139, having a discharge section 140 in which ionization occurs by use of photons, preferably accomplished using a first discharge electrode 104 and a second discharge electrode 114 therein, and a reaction section 142, notably having a plurality of bias/collecting electrodes 206a, 206b, 206c, 206d, 206e therein.

Referring to FIG. 2, the detector body 108 has a first end 110 and a second end 126 with openings and outlets associated with them. A discharge gas inlet 134 is positioned through the detector body 108 proximate the detector body first end 110. The detector body first end 110 may include an first end piece 112 at the detector body first end 110 and a second end piece 128 at the detector body second end 126. The discharge gas inlet 134 may be positioned at the first end 110 of the detector body 108 or near or proximate the first end 110, such as on a side of the detector body 108 near or proximate or adjacent the detector body first end 110. A column inlet 132 is positioned through the detector body 108 proximate its second end 126. The column inlet 132 may be positioned at the second end 126 of the detector body 108 or near or proximate the second end 126, such as on a side. An outlet or vent 144 is also positioned through the detector body 108 proximate its second end 126. The outlet or vent 144 may be positioned at the second end 126 of the detector body 108 or near or proximate the second end 126, such as on a side.

Within the cell 138 of the detector body 108, the discharge section 140 and reaction section 142 are associated with the gas discharge inlet 134 and the outlet or vent 144, respectively, and each is further defined in light of position of the specific electrodes. The discharge section 140 is intermediate the reaction section 142 and the discharge gas inlet 134, while the reaction section 142 is intermediate the discharge section 140 and the outlet 144. As can be appreciated, the ionization source, here the first discharge electrode 104 and the second discharge electrode 114, are positioned in, or at least have exposed surfaces in, the discharge section 140 while the bias/collecting electrodes 206a, 206b, 206c, 206d, 206e are positioned in, or at least have an exposed surface in, the reaction section 142 of the cell 138 of the detector body 108. The first end 106 of the first discharge electrode 104 and the first end 116 of the second discharge electrode 114 are separated from one another sufficient for electrical spark generation. In the preferred embodiment, the first discharge electrode 104 is pointed, or at least of reducing diameter, at its first end 114 to discharge across a gap, which may be at or about 1 mm, to the surface of a ring-type second discharge electrode 114. Alternative methods of photoionization may be used, such as photoionization lamps.

The discharge section 140 and reaction section 142 are further associated with different inner diameters of the cell. The inner diameter of the discharge section 140 is sufficiently smaller than the inner diameter of the reaction section 142 to ensure the discharge gas, ionized by the discharge between the first discharge electrode 104 and the second discharge electrode 114 and to provide the necessary ionization of the constituents of the column gas to provide the electrical output to the various bias/collecting electrodes 206a, 206b, 206c, 206d, 206e. In the reaction section 142, a plurality of spacers 118, such as sapphire spacers, are stacked with the bias/collecting electrodes 206a, 206b, 206c, 206d, 206e, sandwiching a bias/collecting electrodes 206a, 206b, 206c, 206d, 206e between a pair of spacers 118. The sizes of the spacer 118 need not be uniform, and where the bias/collecting electrodes 206a, 206b, 206c, 206d, 206e are not equally spaced the size is not uniform, but the size of each spacer 118 must be sufficient to perform its function within the detector body 108. This stack may be surrounded by an air gap 136 to provide insulation and separation. In the preferred embodiment, each of five bias/collecting electrodes 206a, 206b, 206c, 206d, 206e is sandwiched between one of six sapphire spacers 118. Other conventional components may be included in or about the detector body 108, such as heater blocks installed in the reaction section 142 to heat the interior of the detector body 108 for use in connection with high-boiling compounds.

Referring to FIG. 3, unlike prior art, the present invention utilizes a plurality of combined bias/collecting electrodes 206a, 206b, 206c, 206d, 206e. To accomplish this dual biasing and collecting purpose, each bias/collecting electrode 206a, 206b, 206c, 206d, 206e is in electrical connection with its own bias source 304a, 304b, 304c, 304d, 304e, which is adapted to provide a bias voltage to the associated bias/collecting electrode 206a, 206b, 206c, 206d, 206e. The bias applied to the associated bias/collecting electrode 206a, 206b, 206c, 206d, 206e may be selected based on position within the cell 138. The various bias sources 304a, 304b, 304c, 304d, 304e, associated with the various bias/collecting electrodes 206a, 206b, 206c, 206d, 206e need not supply the same bias to the various bias/collecting electrodes 206a, 206b, 206c, 206d, 206e. As a result of its bias and of its position in the reaction section 142, each bias/collecting electrode 206a, 206b, 206c, 206d, 206e is adapted to, and generates when used, a time-dependent bias/collecting electrode current output 305a, 305b, 305c, 305d, 305e. As can be appreciated, during use, the time-dependent current output 305a, 305b, 305c, 305d, 305e generated at a specific bias/collecting electrode 206a, 206b, 206c, 206d, 206e varies over time in response to the constituents flowing from the column inlet 132, to the bias applied to the particular bias/collecting electrode 206a, 206b, 206c, 206d, 206e, and its position in the cell 138.

The time-dependent bias/collecting electrode current outputs 305a, 305b, 305c, 305d, 305e associated with each bias/collecting electrode 206a, 206b, 206c, 206d, 206e is then converted to a voltage domain by an associated current-to-voltage converter 307a, 307b, 307c, 307d, 307e, which may be an electrometer. Each current-to-voltage converter 307a, 307b, 307c, 307d, 307e has its own input 306a, 306b, 306c, 306d, 306e and output 308a, 308b, 308c, 308d, 308e, wherein the input 306a, 306b, 306c, 306d, 306e is in electrical connection with the associated bias/collecting electrode 206a, 206b, 206c, 206d, 206e and provides the voltage-domain output at its output 308a, 308b, 308c, 308d, 308e. Each current-to-voltage converter 307a, 307b, 307c, 307d, 307e is adapted to, and generates during use, a time-dependent bias/collector electrode voltage 309a, 309b, 309c, 309d, 309e (a time-dependent bias/collector electrode voltage output), based on the associated time-dependent bias/collecting electrode current 305a, 305b, 305c, 305d, 305e.

As can be appreciated, the intensity from each bias/collecting electrode 206b, 206c, 206d, 206e suffers increasing reduction due to the distance between the discharge source at the first discharge electrode first end 106 and second discharge electrode 114 and the particular electrode 206b, 206c, 206d, 206e serving as a bias/collecting electrode. To address the loss of intensity of the time-dependent bias/collecting electrode current outputs 305a, 305b, 305c, 305d, 305e and after current-to-voltage conversion, the time-dependent bias/collector electrode voltage outputs 309a, 309b, 309c, 309d, 309e, and therefore to obtain outputs that have equivalent peak heights, a gain is applied by a gain adjuster 311b, 311c,

311d, 311e to the pathway associated with all but one bias/collecting electrode 206a, 206b, 206c, 206d, 206e, to obtain and output at the gain adjuster output 312b, 312c, 312d, 312e the gain-adjusted time-dependent bias/collector electrode voltage outputs 314ba, 314b, 314c, 314d, 314e of equivalent strength. Preferably, the pathway associated with the first bias/collecting electrode 206a is not subject to the application of a gain. Preferably, the gain adjuster 311b, 311c, 311d, 311e is integrated into an electrometer to provide both gain and current-to-voltage conversion.

The gain to be applied may be the reciprocal of the normalized solid angle value of each bias/collecting electrode 206a, 206b, 206c, 206d, 206e. These normalized solid angle values are obtained ultimately by normalizing the solid angle for each bias/collecting electrode 206a, 206b, 206c, 206d, 206e, resulting in the normalized solid angle for the first bias/collecting electrode 206a being 1.

Since lights emits in all directions, increasing the distance reduces the total number of photons available for ionization. The measurement of the reduction in the number of photons by distance can be expressed by a solid angle which is the measurement of the area exposed to the photon source at a given distance compared with its area projected on the surface of a sphere. The actual formula is $$\text{Solid Angle } \Omega = kS/R^2$$

Where k is the proportionality constant, S is the surface area of the projection onto the sphere, and R is the radius of the sphere. Here, the proportionality constant k is 1 as the medium is air. The surface area S is defined by the exposed interior of the bias/collecting electrode 206a, 206b, 206c, 206d, 206e, which typically will be circular. The radius R of the sphere is defined by the distance between the spark location at first discharge electrode 104 and the second discharge electrode 114 and the perpendicular centerline of the bias/collecting electrode 206a, 206b, 206c, 206d, 206e. So the reduction of the total photons is reversely proportional to the square of the distance if source intensity and project area are constant. The solid angles of the multi collecting PDHID can thus be calculated from the physical dimensions of the detector. Assuming a detector having bias/collecting electrodes 206a, 206b, 206c, 206d, 206e positioned at 18 mm, 23 mm, 28 mm, 33 mm and 38 mm from the spark location, with diameter of 3 mm, the results of use of the formula may be similar to those presented in Table 1, which presented for illustrative purposes.

TABLE 1

Solid angles and responses for multi collecting PDHID

| | Original | | | | Relative | | | |
|---|---|---|---|---|---|---|---|---|
| | | Peak Area (nA · s) | | | | Peak Area | | |
| | Solid Angle (Steradian) | $C_1+$ air | $C_2$ | $C_3$ | Solid Angel | $C_1+$ air | $C_2$ | $C_3$ |
| 206a | 0.0218 | 52.7 | 38.2 | 51.7 | 1.00 | 1.00 | 1.00 | 1.00 |
| 206b | 0.0134 | 34.1 | 26.0 | 35.2 | 0.61 | 0.65 | 0.68 | 0.68 |
| 206c | 0.0090 | 23.3 | 18.9 | 24.7 | 0.41 | 0.44 | 0.49 | 0.48 |
| 206d | 0.0065 | 18.1 | 14.2 | 19.2 | 0.30 | 0.34 | 0.37 | 0.37 |
| 206e | 0.0049 | 14.7 | 11.8 | 15.9 | 0.22 | 0.28 | 0.31 | 0.31 |

Figure 4A:
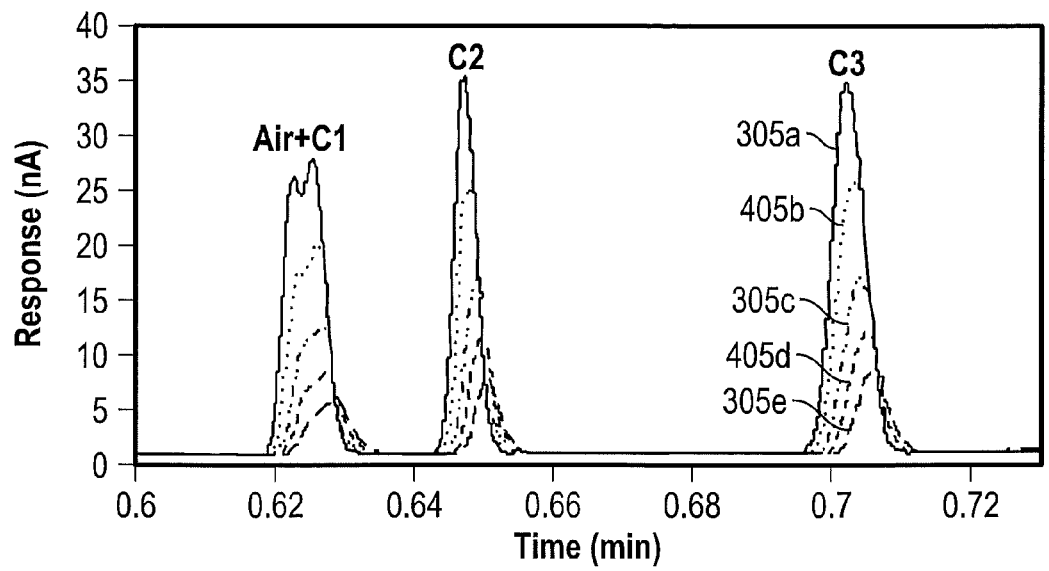
FIG. 4a is an illustration of chromatograms described in the present invention showing, in a current domain, the various current outputs with or converted to positive current absent gain adjustment.
Figure 4B:
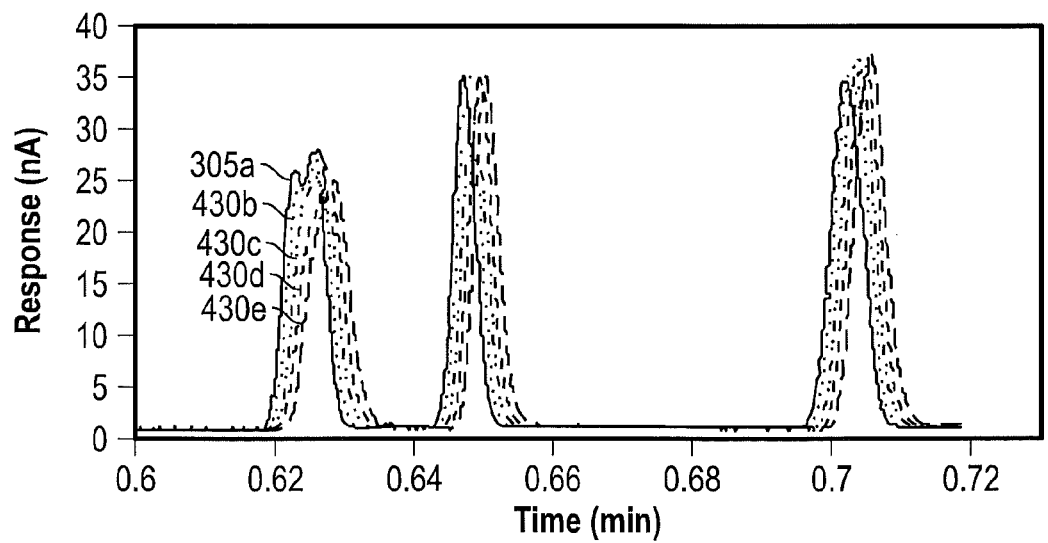
FIG. 4b is illustration of chromatograms described in the present invention showing, in a current domain, the various current outputs with or converted to positive current with gain adjustment.
Figure 4C:
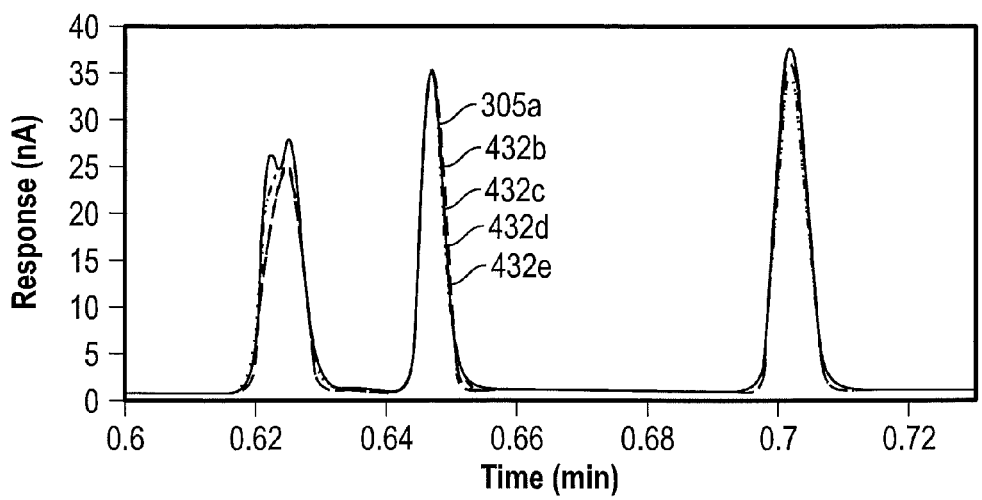
FIG. 4c is illustration of chromatograms described in the present invention showing, in a current domain, the various current outputs with or converted to positive current with gain adjustment and with the time delay eliminated.

Referring to Table 1, the solid angles and each electrode response in peak areas are listed for the data for the chromatograms depicted in FIGS. 4a, 4b and 4c. The original value associated with each electrode 206a, 206b, 206c, 206d, 206e is provided in one data set and the relative (or normalized to the first electrode 206a) values are provided in a second data set. Each data set lists the solid angle, plus the methane, ethane, propane peak areas.

The relative values found in Table 1 for the second data set are the value on each of the bias/collecting electrodes 206a, 206b, 206c, 206d, 206e normalized to the value of the first bias/collecting electrode 206a, were obtained by dividing the solid angle of each second and subsequent bias/collecting electrode 206a, 206b, 206c, 206d, 206e and its peak area value by the value of the first bias/collecting electrode 206a. Thus, for the first bias/collecting electrode 206a all the values are equal to 1, and all the other bias/collecting electrode values are relative to it.

Alternatively, the gain value for each gain adjuster 311b, 311c, 311d, 311e may be the determined by application of the equation $(R_x^2 \times A_1)/(A_x \times R_1^2)$, where $R_x$ is the distance of each bias/collecting electrode 206a, 206b, 206c, 206d, 206e from the first discharge electrode first end 106 and $A_x$ is the cross-sectional area of the cylindrical cell perpendicular to its centerline 139 at each bias/collecting electrode 206a, 206b, 206c, 206d, 206e.

As each bias/collecting electrode 206a, 206b, 206c, 206d, 206e is associated with an adjacent bias/collecting electrode 206a, 206b, 206c, 206d, 206e connected to a potential of oppositive polarity, i.e. the potential applied to each electrode 220 from the first electrode 206a to the last electrode 206e are −55V, 55V, −55V, 55V, −55V respectively, it is necessary to reverse the polarity of the time-dependent first bias/collector electrode voltage output 309a, the gain-adjusted time-dependent third bias/collector electrode voltage output 314c, and any subsequent alternating gain-adjusted time-dependent third bias/collector electrode voltage output 314e. This is accomplished by a voltage polarity inverter 318a, 318c, 318e for each of the members of the identified group of bias/collecting electrodes 206a, 206c, 206e. Each voltage polarity inverter has an input 316a, 316c, 316e, in electrical connection with the first current-to-voltage converter 307 and, if present, the third and alternating subsequent gain adjusters 311b, 311c, 311d, 311e, and has an output 320a, 320c, 320e. Each voltage polarity inverter 318a, 318c, 318e is adapted to and generates at its output 320a, 320c, 320e a polarity-inverted time-dependent bias/collecting electrode voltage 322a, 322c, 322e (a polarity-inverted time-dependent bias/collecting electrode voltage output) associated with its input 316a, 316c, 316e and therefore associated with a particular electrode 206a, 206c, 206e. The voltage polarity inverter 318a, 318c, 318e may be also be incorporated into an electrometer and accomplished by utilizing the negative electrometer input for the first alternating group 206a, 206c, 206e of bias/collecting electrodes and the positive electrometer input for the second group of bias/collecting electrodes 206b, 206d.

As five voltage outputs 322a, 314b, 322c, 314d, 322e exist in connection with the eluted sample, providing five peaks of equivalent, but not necessarily equal value, for each constituent, with separate times based on the position of the bias/collecting electrode 206a, 206b, 206c, 206d, 206e, it is necessary to eliminate the time delay among the common peaks to provide an intelligent output. Thus, next, a time-dependent voltage processor 326 is provided which has an input 324a, 324b, 324c, 324d, 324e and output 328a, 328b, 328c, 328d, 328e associated with each bias/collecting electrode 206a, 206b, 206c, 206d, 206e. At each input 324a, 324b, 324c, 324d, 324e, the time-dependent voltage processor 326 receives a polarity-inverted time-dependent bias/collecting electrode voltage output 322a, 322c, 322e or a gain-adjusted time-dependent bias/collecting electrode voltage output 314b, 314d associated with the various bias/collecting electrodes 206a, 206b, 206c, 206d, 206e. The time-dependent voltage processor 326 is thus either in electrical connection with a gain adjuster 311b, 311d or in connection with a voltage polarity inverter 318a, 318c, 318e. The time-dependent voltage process 326 is adapted to determine and reposition, and in operation determines and repositions, the time-dependent bias/collector electrode voltage output(s) 314b, 314d and the gain-adjusted time-dependent bias/collector electrode voltage output(s) 322a, 322c, 322e to eliminate the delay time between the time-dependent bias/collector electrode voltage output(s) 314b, 314d and the gain adjusted time-dependent bias/collector electrode voltage output(s) 322a, 322c, 322e. The time-dependent voltage processor 326 is adapted to obtain a single chromatogram based on all outputs received by determining, and in operation determines, the average output 330a based on all inputs, including by adding all input values for each point in time and dividing by the resultant sum by the number of inputs used to obtain an average output value for each point in time, in either the voltage or current domain, and which may be displayed visually on a monitor or a printout, and/or which may be stored for later use.

Thus, a method of analyzing a sample compound may comprise the steps of providing the structural elements of the detector, flowing the sample compound, obtaining and correlating the output, and generating a single output. This may be accomplished by first providing a detector body 108 having an internal elongated cylindrical cell 138, providing a first discharge electrode 104 in the detector body 108, providing a second discharge electrode 116 in the detector body 108 separated from the first discharge electrode 104 sufficient for electrical spark generation, providing a first bias/collecting electrode 206a in the detector body 108 in electrical communication with a first bias source 304a to generate a time-dependent first bias/collecting electrode current 305a in response to constituents flowing through the detector body 108, and providing a second bias/collecting electrode 206b in the detector body in electrical communication with a second bias source 304b to generate a time-dependent first bias/collecting electrode current 305b in response to the constituents or compounds in a sample flowing through the detector body 108. The sample may flow as an eluent from a gas chromatography column. Using this method, the current generated at each combined bias/collecting electrode is converted to voltage, namely generating at a first current-to-voltage converter 307a a time-dependent first bias/collector electrode voltage 309a based on the time-dependent first bias/collecting electrode current 305a and generating at a second current-to-voltage converter 307b a time-dependent second bias/collector electrode voltage 309b based on the time-dependent second bias/collecting electrode current 305b. It is then necessary to ensure the time-dependent electrode voltages, which have a peak for each compound, associated with its ionization potential, displayed at the time the compound reaches the bias/collecting electrode, are considered with the proper ionization potential, which necessarily is positive, but, depending on biasing, particularly for the odd-numbered combined bias/collecting electrodes, will be generated as a negative current. Thus, the method includes generating at a voltage polarity inverter 318a a polarity-inverted time-dependent second bias/collecting electrode voltage 322a by altering the value of time-dependent first bias/collector electrode voltage 314a from negative to positive. To address the appreciable decrease in intensity resulting from the increasing distance of each combined bias/collecting electrode from the location of the first combined bias/collecting electrode 206a, it is necessary that a gain adjustment be applied to all but one combined bias/collecting electrode (preferably the first combined bias/collecting electrode). Therefore, the method includes applying a gain at a gain adjuster 311b to the time-dependent second bias/collector electrode voltage 309b to generate a gain-adjusted time-dependent second bias/collector electrode voltage 314b. To address the appreciable delay in time resulting from the increasing distance of each combined bias/collecting electrode of each combined bias/collecting electrode from the location of the first combined bias/collecting electrode 206a, it is necessary to the time delay associated with each combined bias/collecting electrode be identified and eliminated. Thus, the method includes, determining and eliminating the delay time between the polarity-inverted time-dependent first bias/collector electrode voltage output 322a and the gain-adjusted time-dependent second bias/collector electrode voltage output 314b to generate a time-shifted gain-adjusted time-dependent second bias/collector electrode voltage output. With this intensity-correcting and time-corrected data, an average can be obtained and displayed for use. The method therefore includes determining a time-dependent average output from the polarity-inverted time-dependent first bias/collector electrode voltage output 314a and the time-shifted gain-adjusted time-dependent second bias/collector electrode voltage output, and displaying that time-dependent average output.

In another embodiment, a sample compound may be analyzed, and these goals may be accomplished, by the steps of providing a detector body 108 having an internal elongated cylindrical cell 138, providing a first discharge electrode 104 and a second discharge electrode 216 in the detector body 108 separated from the first discharge electrode first end 106 sufficient for electrical spark generation; transmitting a time-dependent first bias/collecting electrode current 305a from a first bias/collecting electrode 206a in the detector body in electrical communication with a first bias source 304a; transmitting a time-dependent second bias/collecting electrode current 305b from a second bias/collecting electrode 206b in the detector body in electrical communication with a second bias source 304b; passing the time-dependent first bias/collecting electrode current 305a through a first current-to-voltage converter 307a and generating a time-dependent first bias/collector electrode voltage 309a; passing the time-dependent second bias/collecting electrode current 305b through a second current-to-voltage converter 307b and generating a time-dependent second bias/collector electrode voltage 309b; passing the time-dependent first bias/collector electrode voltage 314a through a voltage polarity inverter 318a and generating a polarity-inverted time-dependent second bias/collecting electrode voltage 322a by altering the value from negative to positive; increasing the gain of the time-dependent second bias/collector electrode voltage 309b and generating a gain-adjusted time-dependent second bias/collector electrode voltage 314b; determining and eliminating the delay time between the polarity-inverted time-dependent first bias/collector electrode voltage output 322a and the gain-adjusted time-dependent second bias/collector electrode voltage output 314b to generate a time-shifted gain-adjusted time-dependent second bias/collector electrode voltage output; determining a time-dependent average output from the polarity-inverted time-dependent first bias/collector electrode voltage output 314a and the time-shifted gain-adjusted time-dependent second bias/collector electrode voltage output; and displaying the time-dependent average output, which will preferably be displayed as Ionization Potential (IP) with respect to elapsed time.

Alternatively, the method may be accomplished by obtaining outputs incident to the flow of the sample, eliminating the time delay, adjusting intensity, and determining and displaying an average time-delay eliminated intensity adjusted time-dependent output. Accomplishing this may include obtaining a plurality of time-dependent outputs, where each of the plurality of time-dependent outputs associated with a voltage-biased bias/collecting electrode is positioned in the reaction section of a gas detector, and where each of the plurality of time-dependent outputs has an output strength intensity compared to its baseline, and where the gas detector has a first discharge electrode with a first end and an internal open cylindrical cell. The method then includes eliminating the time delay among the plurality of time-dependent outputs and adjusting the intensity of each of the time-dependent outputs by the result of the equation $(R_x^2 \times A_1)/(A_x \times R_1^2)$, where $R_x$ is the distance of the voltage-biased bias/collecting electrode 206a from the first discharge electrode first end 106 and $A_x$ is the cross-sectional area of the cylindrical cell 138 perpendicular to its centerline 139 at the bias/collecting electrode 206a and where $R_1$ is the distance of the first bias/collecting electrode 206a from the first discharge electrode first end 106 and $A_1$ is the cross-sectional area of the cylindrical cell 138 perpendicular to its centerline 139 at the first bias/collecting electrode 206. Then, the method includes determining an average time-delay eliminated intensity adjusted time-dependent output, and displaying the average time-delay eliminated intensity adjusted time-dependent output.

Figure 6:
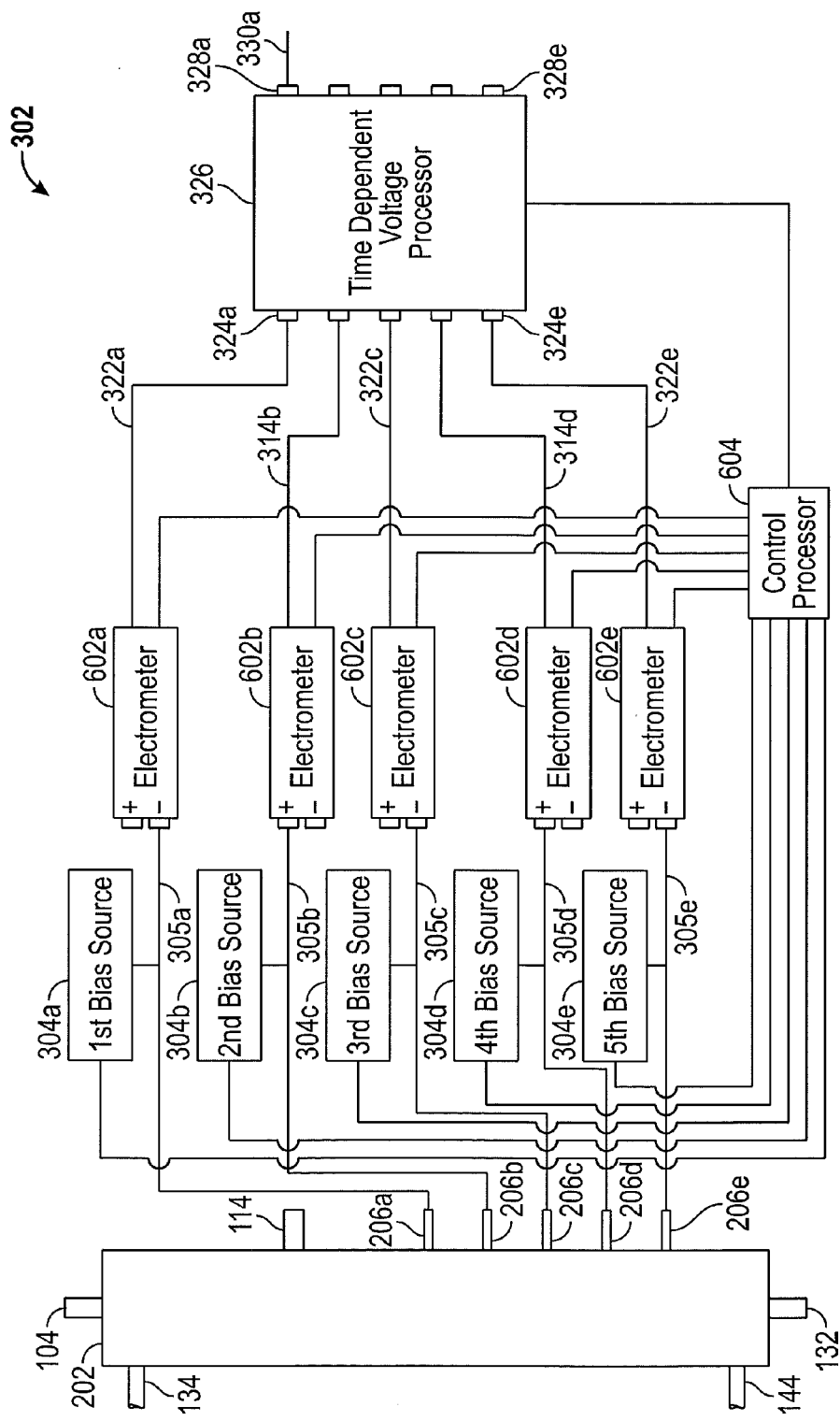
FIG. 6 is an alternative illustration of a pulsed-discharge detector system using the disclosed pulsed-discharge detector.

In operation, a discharge gas enters the detector through the gas discharge (or first) inlet 134, at the top of the cell 138 of the detector 202, which it is ionized in the discharge section 140 by the electrical spark between the first discharge electrode 104 and the second discharge electrode 114. A sample gas flows into the detector 202 from column inlet 132, likely from a chromatographic column (not shown) into the reaction section 142 of the detector 202 in a direction counter to the flow of the discharge gas from the discharge gas inlet 134. Referring to FIG. 6, after detection at the bias/collecting electrodes 206a, 206b, 206c, 206d, 206e, the combined gases exit the detector 202 via outlet or vent 144 and each output 305a, 305b, 305c, 305d, 305e provided to an electrometer 602a, 602b, 602c, 602d, 602e, which is configured to provide the necessary output, including the current-to-voltage conversion, any needed gain adjustment, and any needed voltage polarity inversion, to the time-dependent voltage processor 326. The output of the time-dependent voltage processor 326 is then outputted to a computer system for display or storage, such as a computer, portable electronic device, printer or media storage. Alternatively, after elimination of the time delay, the time-dependent voltage processor 326 may output the time-corrected time-dependent bias/collector electrode voltage associated with each bias/collecting electrode 206a, 206b, 206c, 206d, 206e which may be simultaneously displayed or stored for future use.

Thus, the first current-to-voltage converter 307a and the first polarity inverter 318a are incorporated into the first electrometer 602a and the second current-to-voltage converter 307b and the first gain adjuster 311b are incorporated into a second electrometer 602b. Similarly, the third current-to-voltage converter 307c, the second gain adjuster 311c and the second polarity inverter 318c are incorporated into the third electrometer 602c. The fourth current-to-voltage converter 307d, and the third gain adjuster 311d are incorporated into fourth electrometer 602d. The fifth current-to-voltage converter 307e, the fourth gain adjuster 311e and the third polarity inverter 318c are incorporated into the fifth electrometer 602e.

Additionally, a control processor 604 may be incorporated to avoid manual setting of various equipment, adapted to control, and in operation controlling, the output of each first bias source 304a, 304b, 304c, 304d, 305e, adapted to control, and in operation controlling, each first electrometer 602a, 602b, 602c, 602d, and 602e (or the components identified as being incorporated therein), and adapted to control, and in operation controlling, the time-dependent voltage processor 326.

Referring to FIGS. 4a, 4b and 4c, chromatograms of methane, ethane, and propane obtained by the multi-electrode PDHID in alternate collecting potential mode, following polarity inversion, are displayed with and without application of the various components and steps of the present invention to illustrate the need for each action. As the methane peak has a small amount of air co-elute with it, the first peak is slightly split.

FIG. 4a, depicted in a current domain, reflects the first, third and fifth time dependent bias/collecting electrode current outputs 305a, 305c, 305e with polarity inversion to produce first, third and fifth polarity-inverted time dependent bias/collecting electrode current outputs 405a, 405c, 405e and the second and fourth time-dependent bias/collector electrode current outputs 305b, 305d, which are positive, without gain adjustment and prior to any action by the time-dependent voltage aggregator to eliminate time delays and aggregate the voltage output. The lack of a common intensity height (from a lack of gain adjustment) and time delay are evident from the horizontal positions of the various peaks for air, $C_1$, $C_2$ and $C_3$. Various corrections are therefore needed to render the first, third and fifth polarity-inverted time dependent bias/collecting electrode current outputs 405a, 405c, 405e and the second and fourth time-dependent bias/collector electrode current outputs 305b, 305d usable.

As depicted in FIG. 4a, there is a loss of intensity for each subsequent output, evident by positioning the baseline of the first, third and fifth polarity-inverted time dependent bias/collecting electrode current outputs 405a, 405c, 405e and second and fourth time-dependent bias/collector electrode current outputs 305b, 305d to a common baseline at 1.0 nA. The original baselines of the first, third and fifth polarity-inverted time dependent bias/collecting electrode current outputs 405a, 405c, 405e and second and fourth time-dependent bias/collector electrode current outputs 305b, 305d are respectively 2.2 nA, 1.6 nA, 0.45 nA, 0.30 nA and 0.11 nA. The intensities are thus attenuated, as can be seen, from the first bias/collecting electrode 206a, having the highest intensity, to the last bias/collecting electrode 206e, having the lowest intensity. A gain must therefore applied to each output to obtain a waveform of common intensity.

Referring to FIG. 4b, as evidenced by application of a gain, even in the current domain, there still exists a time-delay among the various outputs. Application of the gain adjustment to the third and fifth polarity-inverted time dependent bias/collecting electrode current outputs 405c, 405e and second and fourth time-dependent bias/collector electrode current outputs 305b, 305d produces gain-corrected second, third, fourth, and fifth outputs 430b, 430c, 430d, 430e waveforms having equivalent intensities for each of the time-dependent voltage outputs associated with a specific bias/collecting electrode 206a, 206b, 206c, 206d, 206e. The time delay, however, remains evident. This peak delay is to be expected, since the ionized sample reaches the first electrode 206a first, then passes to successive electrodes 206b, 206c, 206d and 206e in sequence, forming a delay time between the electrodes 206a, 206b, 206c, 206d, 206e. The delay time depends on how fast the sample is moving inside the detector cell 138, which is in turn determined by cell size, flow rate, and temperature.

The chromatograms in FIG. 4c illustrate the elimination of the time delay between first, third and fifth polarity-inverted time dependent bias/collecting electrode current outputs 405a and gain-corrected second, third, fourth, and fifth outputs 430b, 430c, 430d, 430e where the system includes a total flow (discharge+column) of 35 mL/min at 50° C. With these conditions and a known cell size, the delay time between the first electrode 206a and the final electrode 206e can be calculated, in the provided example 278 milliseconds. Where the electrodes 206a, 206b, 206c, 206d, 206e are evenly spaced, each of the successive electrodes 206b, 206c, 206d, 206e, has a response delay, relative to the previous electrode, of about 69.5 milliseconds. Similarly, if the electrodes 206a, 206b, 206c, 206d, 206e are not equally spaced, the delay would be proportional to the position of the successive electrodes 206b, 206c, 206d, 206e relative to the delay between the first electrode 206a and the last electrode 206e and the position of the electrode 206a, 206b, 206c, 206d, 206e relative to those two. Each subsequent chromatogram, the chromatograms for the gain-corrected second, third, fourth, and fifth outputs 430b, 430c, 430d, 430e, may be advanced by the calculated delay time, such as by computer software, to provide a resulting time-and-gain adjusted second, third, fourth, and fifth outputs 432b, 432c, 432d, 432e, such as that illustrated in FIG. 4c, wherein the chromatograms generated from each electrode 206a, 206b, 206c, 206d, 206e closely overlap and the time-corrected time-dependent bias/collector electrode outputs may be averaged, preferably in a voltage domain.

Figure 5:
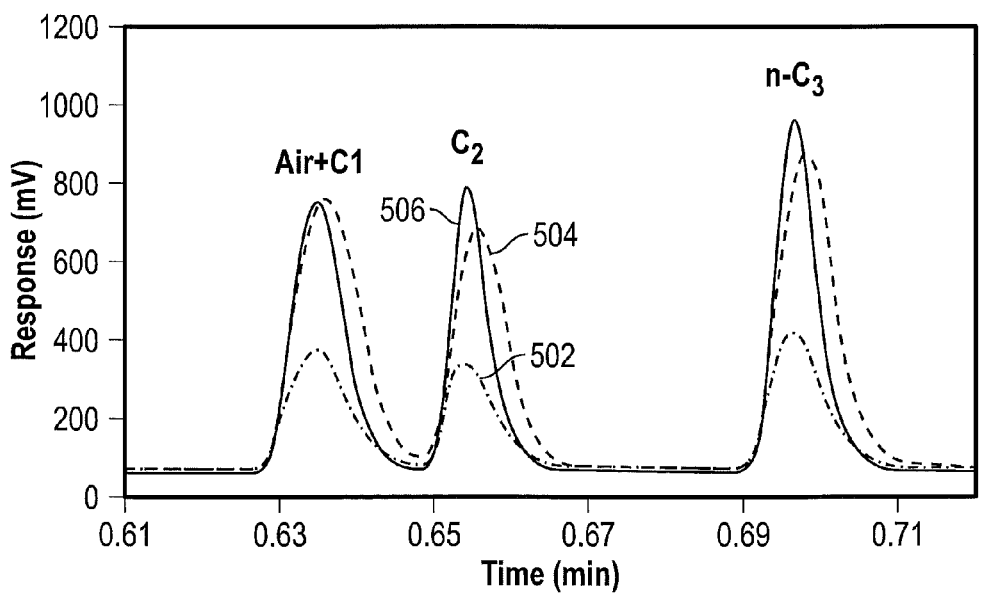
FIG. 5 is illustration of chromatograms described in the present invention showing, in a voltage domain, the final time dependent average ouput compared to chromatograms which would have resulted absent gain adjustment or, even with gain adjustment, absent time delay eliminate.

Referring to FIG. 5, chromatograms in a voltage-domain provide an illustration of a chromatogram based on an average of the raw (no gain or intensity adjustment, no time adjustment) data 502, a chromatogram based an average of intensity-calibrated (gain adjusted) data 504, and a chromatogram 506 based an average of intensity and delay calibrated data. The chromatogram based on an average of the raw data 502 is similar to one from a standard single-collecting PDHID, with the peaks showing some degree of asymmetry. The chromatogram from intensity-calibrated data (dot line) 504 shows improved symmetry, but the peaks are wider. Finally, the chromatogram 506 resulting from intensity and delay calibrated data (solid) shows peaks which are both symmetric and narrow. The peak half-widths for ethane ($C_2$) in FIG. 5 are 391, 412, and 270 milliseconds for the original, intensity-calibrated, and intensity- and delay-calibrated data, respectively. Calibration reduces the ethane peak half-width from 391 milliseconds to 270 milliseconds—a difference of 121 milliseconds, or 31%, which is a significant improvement.

TABLE 2

Multi collecting PDHID sensitivity

| Electrode | Noise | Peak Height | Signal to noise | MDQ (ppb, s/n = 3) |
|---|---|---|---|---|
| First (206a) | 0.086 | 2.70 | 31.26 | 4.8 |
| Second (206b) | 0.090 | 2.70 | 29.94 | 5.0 |
| Third (206c) | 0.148 | 2.70 | 18.19 | 8.2 |
| Fourth (206d) | 0.142 | 2.70 | 19.05 | 7.9 |
| Fifth (206e) | 0.158 | 2.70 | 17.12 | 8.8 |
| Cumulative (206a-e) | 0.245 | 13.5 | 55.1 | 2.7 |
| one-collector | 0.140 | 2.30 | 16.43 | 9.1 |

Further, the use of multiple combined bias/collecting electrodes provides comparative improved sensitivity. The pulsed discharge helium ionization detector is one of the most sensitive detectors for gas chromatography—about 10 times more sensitive than the commonly used flame ionization detector (FID). The PDHID's ionization percentage is 0.007% which is about 100 times higher an FID's. Even though the noise in a PDHID is approximately 10 times higher than an FID's, the net sensitivity increase for the PDHID is about 10 times. PDHID sensitivity with multiple bias/collecting electrodes is even higher. Table 2 shows the test results for a 50 ppb Freon peak, listing the noise level, peak height, signal to noise ratio, and minimum detectable quantity (MDQ) for each electrode, as well as the additive results. For comparison, single-collecting PDHID data are listed in the last row of the table. As indicated, the peak heights for the bias/collecting electrodes 206a, 206b, 220c, 206d, and 206e after intensity calibration are about 2.7, with noise levels ranging from 0.086 to 0.158. This yields a signal-to-noise ratio in the range of 17-31 and an MDQ of 4.8-8.8 ppb. Combining these in an additive chromatogram gives a peak height of 13.5 with a noise level of 0.245. The resultant a signal-to-noise ratio of 55.1 and MDQ of 2.7 pp indicate a sensitivity of 2-3 times higher for each electrode and 3.5 times higher than a single-collecting PDHID. In the additive chromatogram, the output or peak height combination is a simple addition process, while the noise level is not; when chromatograms are added together, there is some degree of the noise cancellation.

Since the peak heights listed in Table 2 have been intensity-calibrated with respect to the time dependent bias/collecting electrode voltage of bias/collecting electrode 206a such that the peak heights are equivalent, the values do not reflect the decreasing peak height as the electrode number (and distance from the discharge) increases. Intensity calibration is performed before the peaks are added together to ensure that each wave has the same weight in the additive chromatogram, providing best noise cancellation result. Thus, with this calibration, the noise level and the peak height will change, but the signal-to-noise ratio remains constant. While it is not reasonable to compare this intensity-calibrated additive chromatogram with one from a single-collecting PDHID, a comparison can be obtained by comparing the actual current collected by adding the actual uncalibrated peak height from each electrode for the 50 ppb Freon 11 sample, a result of 0.528 pA, to the single-collecting PDHID value of 0.230 pA—an increase by a factor of 2.3.

Figure 1:
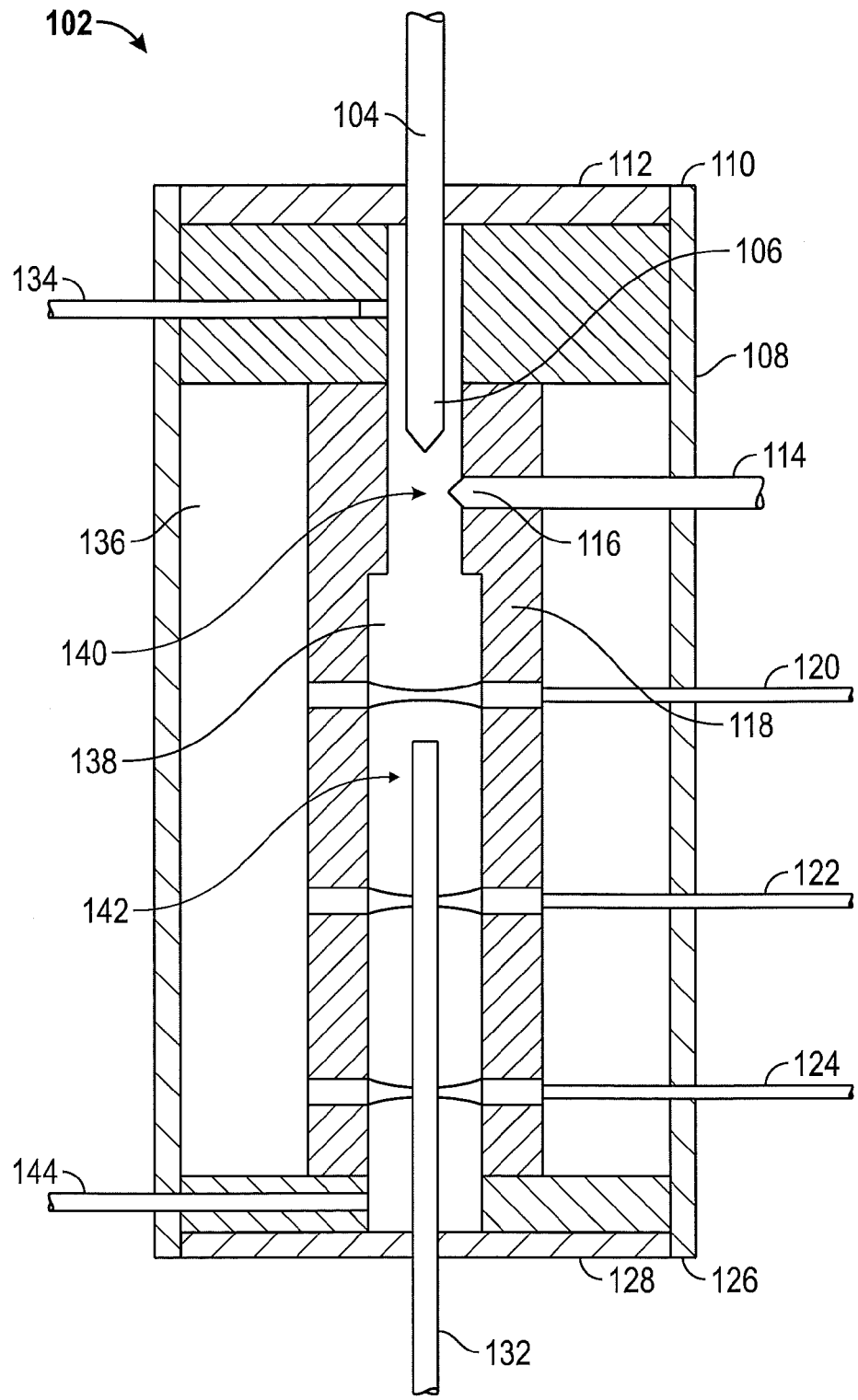
FIG. 1 is an illustration of a pulsed-discharge detector known in the art.

Referring to FIG. 1, in the prior art, a pulsed discharge helium ionization detector 102 included only one collector electrode 122 and one or more bias electrodes 120, 124. A single collecting detector 102 might be configured so that the bias electrodes 120, 124 would be connected to a −200 V bias voltage and the collector electrode 122 connected to an electrometer.

The increased sensitivity of the pulsed discharge helium ionization detector 202 with multiple combined bias/collecting electrodes 206 is a result of its structural differences from a single bias/collecting electrode 122. A typical single-collecting PDHID 102, such as that depicted in FIG. 1, has a ring-type bias/collecting electrode 122 in the middle of the detector cell 138 intended to collect all electrons (or positive ions) created in the cell 138. The bias voltage applied on the bias electrodes 120, 124 creates an electrical field which pushes the electrons toward the bias/collecting electrode 122. While ideally every electron generated in the detector cell 138 can be collected, in reality only a portion are. Some are lost through recombination reactions during their travel. The longer the distance travelled, the higher the likelihood that the electron will be recombined instead of collected. Referring to the instant invention depicted in FIG. 2, as the pulsed discharge helium ionization detector 202 with multiple combined bias/collecting electrodes 206a, 206b, 206c, 206d, 206e has more bias and bias/collecting electrodes in the same cell 138, the distance between the combined bias/collecting electrodes 206a, 206b, 206c, 206d, 206e is reduced, reducing the travel time of the charged particles and consequently increasing the collecting efficiency and intensity.

Moreover, as the single-collecting PDHID 102 collects only electrons (the positive ions are discharged on the bias electrode 120, 124), positive ions make no contribution to the output. This cannot be cured with a conventional PDHID. When a PDHID 102 is alternatively biased to collect positive ions, the electrons are instead discharged, providing no contribution to the output. Thus, in either configuration of the single-collecting PDHID 102, some of the charged particles are not being collected. The fact that the pulsed discharge helium ionization detector 202 with multiple combined bias/collecting electrodes 206a, 206b, 206c, 206d, 206e collects both electrons and positive ions is enough by itself to increase the output intensity, including by the cumulative benefit of collecting both ions and electrons and as a result of increased collecting efficiency, the latter providing a further 30% increase in value.

The interior configuration of the collecting potential field inside the cell 138 of the detector 202 may be selected based on arrangement, polarity and strength, among other factors. The arrangement includes linear arrangement where the potentials applied to electrode are linear increase or decrease, curved where the potential is curved, and alternate where the potential polarity is alternated along detector cell. For linear and curved, it can also be configured as positive potential or negative potential. The positive potential is defined as where the potential from discharge to last electrode 206e is positive, and vice versa. The last electrode 206e collects positive ions in positive potential mode, and collects electrons in negative potential mode. As show in FIG. 1, the typical PDHID 102 uses an alternate potential configuration. Both bias electrodes 120, 124 apply a biasing voltage of −200V while the bias/collecting electrode 122, positioned intermediate, is the ground potential, so the top section is in negative potential and bottom section is in positive potential. The potential strengths in both sections are equal at 200 V/cm. This configuration requires lower voltage for a high potential strength, but may cause peak distortion in some cases because the electrons are collected from two different sections. The pulsed discharge helium ionization detector 202 with multiple combined bias/collecting electrodes 206a, 206b, 206c, 206d, 206e instead uses a wholly alternative potential arrangement for the performance test. The potential applied to each electrode 220 from the first electrode 206a to the last electrode 206e are −55V, 55V, −55V, 55V, −55V respectively, thus providing potential strengths of 200 V/cm equally between the bias/collecting electrodes 206a, 206b, 206c, 206d, 206e, the same as the typical PDHID 102. Thus, the arrangement of the pulsed discharge helium ionization detector 202 with multiple combined bias/collecting electrodes 206 provides less interference from adjacent sections and can collect more current than the linear arrangement.

The terms and expressions which have been employed in the foregoing specification are used therein as terms of description and not of limitation, and there is no intention, in the use of such terms and expressions, of excluding equivalents of the features shown and described or portions thereof.

We claim:

1. A detector system, comprising
a) a detector body (108),
  1) said detector body (108) having a first end (110) and a second end (126),
  2) said detector body (108) defining an open cylindrical cell (138) between said first end (110) and said second end (126), said cylindrical cell (138) having a centerline (139),
  3) said detector body (108) having a discharge gas inlet (134) therethrough proximate said first end (110),
  4) said detector body (108) having a column inlet (132) therethrough proximate said second end (126),
  5) said detector body (108) having an outlet (144) therethrough proximate said second end (126);
b) said cell (138) having a discharge section (140) and a reaction section (142),
  1) said discharge section (140) intermediate said reaction section (142) and said discharge gas inlet (134),
  2) said reaction section (142) intermediate said discharge section (140) and said outlet (144);
c) a first discharge electrode (104),
  1) said first discharge electrode (104) having a first end (106) having an exposed surface in said cell (138) of said detector body (108) in said discharge section (140);
d) a second discharge electrode (114),
  1) said second discharge electrode (114) having a first end (116) having an exposed surface in said cell (138) of said detector body (108) in said discharge section (140),
  2) said second discharge electrode first end (116) separated from said first discharge electrode first end (106) sufficient for electrical spark generation;
e) a first bias/collecting electrode (206a) having an exposed surface in said cell (138) of said detector body (108) in said reaction section (142)
  1) a first bias source (304a) adapted to provide a first bias voltage to said first bias/collecting electrode (206a),
  2) said first bias/collecting electrode (206a) adapted to generate a time-dependent first bias/collecting electrode current output (305a);
f) a second bias/collecting electrode (206b) having an exposed surface in said cell (138) of said detector body (108) in said reaction section (142);
  1) a second bias source (304b) adapted to provide a second bias voltage to said second bias/collecting electrode (206b);
  2) said second bias/collecting electrode (206b) adapted to generate a time-dependent second bias/collecting electrode current output (305b);
g) a first current-to-voltage converter (307a),
  1) said first current-to-voltage converter (307a) adapted to generate a time-dependent first bias/collector electrode voltage output (309a) based on said time-dependent first bias/collecting electrode current output (305a);
h) a second current-to-voltage converter (307b),
  1) said second current-to-voltage converter (307b) adapted to generate a time-dependent second bias/collector electrode voltage output (309b) based on said gain-adjusted time-dependent second bias/collecting electrode current output (305b);
i) a first voltage polarity inverter (318b),
  1) said first voltage polarity inverter (318b) adapted to generate a polarity-inverted time-dependent first bias/collecting electrode voltage output (322b) by altering the value of said time-dependent first bias/collector electrode voltage output (309b) from negative to positive;

j) a first gain adjuster (311b)
   1) said first gain adjuster (311b) adapted to generate a gain-adjusted time-dependent second bias/collecting electrode voltage output (314b) by multiplying said time-dependent second bias/collecting electrode voltage output (309b) by a first gain value;
k) a time-dependent voltage aggregator (326),
   1) said time-dependent voltage aggregator (326) adapted to determine and eliminate the delay time between said polarity-inverted time-dependent first bias/collector electrode voltage output (322a) and said gain-adjusted time-dependent second bias/collector electrode voltage output (314b) to generate a time-shifted gain-adjusted time-dependent second bias/collector electrode voltage output,
   2) said time-dependent voltage aggregator (326) adapted to determine a time-dependent average output from said polarity-inverted time-dependent first bias/collector electrode voltage output (314a) and said time-shifted gain-adjusted time-dependent second bias/collector electrode voltage output,
   3) said time-dependent voltage aggregator (326) adapted to output said time dependent average output.

2. The detector system of claim 1, wherein said first end (106) of said first discharge electrode (104) is pointed.

3. The detector system of claim 1, wherein said second discharge electrode (114) is constructed as a ring-type electrode.

4. The detector system of claim 1, wherein said gain value for each gain adjuster is determined by $(R_x^2 \times A_1)/(A_x \times R_1^2)$, where $R_x$ is the distance of said bias/collecting electrode (206a) from said first discharge electrode first end (106) and $A_x$ is the cross-sectional area of the cylindrical cell (138) perpendicular to its centerline (139) at said bias/collecting electrode (206a) and where $R_1$ is the distance of said first bias/collecting electrode (206a) from said first discharge electrode first end (106) and $A_1$ is the cross-sectional area of the cylindrical cell (138) perpendicular to its centerline (139) at said first bias/collecting electrode (206).

5. The detector system of claim 1 further comprising sapphire spacers (118) between said bias/collecting electrodes (206a, 206b, 206c, 206d, 206e).

6. The detector system of claim 1 wherein said cell (138) is elongated.

7. The detector system of claim 1 wherein said first current-to-voltage converter (307a) and said first polarity inverter (318a) are incorporated into a first electrometer (602a) and said second current-to-voltage converter (307b) and said first gain adjuster (311b) are incorporated into a second electrometer (602b).

8. The detector system of claim 7 further comprising:
a control processor (604), said control processor adapted to control the output of said first bias source (304a), adapted to control said first electrometer (602a), adapted to control said second bias source (304b), adapted to control said second electrometer (602b) and adapted to control said time-dependent voltage processor (326).

9. The detector system of claim 1, wherein said voltage polarity inverter (318b) is incorporated into said first current-to-voltage converter (310b) and where said input (316b) is a negative input of said current-to-voltage converter (318b).

10. The detector system of claim 1, further comprising
a) a third bias/collecting electrode (206c) having an exposed surface in said cell (138) of said detector body (108) in said reaction section (142)
   1) a third bias source (310c) adapted to provide a third bias voltage to said third bias/collecting electrode (206c),
   2) said third bias/collecting electrode (206c) adapted to generate a time-dependent third bias/collecting electrode current output (305c);
b) a third current-to-voltage converter (307c),
   1) said third current-to-voltage converter (307c) having a third current-to-voltage converter input (306c) and a third current-to-voltage converter output (308c),
   2) said third current-to-voltage converter (307c) in electrical connection with third bias/collecting electrode (206c);
   3) said third current-to-voltage converter (307c) adapted to generate a time-dependent third bias/collector electrode voltage output (309c) based on said time-dependent third bias/collecting electrode current output (305c);
c) a second gain adjuster (311c)
   1) said second gain adjuster (311c) adapted to generate a gain-adjusted time-dependent third bias/collecting electrode voltage output (314c) by multiplying said time-dependent third bias/collecting electrode voltage output (309c) by a second gain value;
d) a second voltage polarity inverter (318c),
   1) said second voltage polarity inverter (318c) having an input (316c) and an output (320c),
   2) said second voltage polarity inverter input (316e) in electrical connection with said second gain adjuster (311c),
   3) said second voltage polarity inverter (318c) adapted to receive at said input (316c) said gain-adjusted time-dependent third bias/collector electrode voltage output (314c)
   4) said second voltage polarity inverter (318c) adapted to output at said voltage polarity inverter output (320c) a polarity-inverted time-dependent third bias/collecting electrode voltage (322c) by altering the value of time-dependent third bias/collector electrode voltage output (314c) from negative to positive;
e) a fourth bias/collecting electrode (206d) having an exposed surface in said cell (138) of said detector body (108) in said reaction section (142)
   1) a fourth bias source (310d) adapted to provide a fourth bias voltage to said fourth bias/collecting electrode (206d),
   2) said fourth bias/collecting electrode (206d) adapted to generate a time-dependent fourth bias/collecting electrode current output (305d);
f) a fourth current-to-voltage converter (307d),
   1) said fourth current-to-voltage converter (307d) having a fourth current-to-voltage converter input (306d) and a fourth current-to-voltage converter output (308d),
   2) said fourth current-to-voltage converter (308d) in electrical connection with fourth bias/collecting electrode (206d);
   3) said fourth current-to-voltage converter (307d) adapted to generate a time-dependent fourth bias/collector electrode voltage output (309d) based on said time-dependent fourth bias/collecting electrode current output (305d);
g) a third gain adjuster (306c)
   1) said third gain adjuster adapted to generate a gain-adjusted time-dependent fourth bias/collecting electrode voltage output (314c) by multiplying said time-

17 dependent fourth bias/collecting electrode voltage output (309*b*) by a third gain value.
h) a fifth bias/collecting electrode (206*d*) having an exposed surface in said cell (138) of said detector body (108) in said reaction section (142)
   1) a fifth bias source (310*e*) adapted to provide a fifth bias voltage to said fifth bias/collecting electrode (206*e*),
   2) said fifth bias/collecting electrode (206*e*) adapted to generate a time-dependent fifth bias/collecting electrode current output (305*e*);
i) a fifth current-to-voltage converter (307*e*),
   2) said fifth current-to-voltage converter (307*e*) having a fifth current-to-voltage converter input (306*e*) and a fifth current-to-voltage converter output (308*e*),
   3) said fifth current-to-voltage converter (308*e*) in electrical connection with fifth bias/collecting electrode (206*e*);
   4) said fifth current-to-voltage converter (307*e*) adapted to generate a time-dependent fifth bias/collector electrode voltage (309*e*) based on said time-dependent fifth bias/collecting electrode current (305*e*);
j) a fourth gain adjuster (306*c*)
   2) said fourth gain adjuster adapted to generate a gain-adjusted time-dependent fifth bias/collecting electrode voltage output (314*c*) by multiplying said time-dependent fifth bias/collecting electrode voltage output (309*b*) by a fourth gain value.
k) a third voltage polarity inverter (318*e*),
   1) said second voltage polarity inverter (318*e*) having an input (316*e*) and an output (320*e*),
   2) said third voltage polarity inverter input (316*e*) in electrical connection with said fifth gain adjuster (311*e*),
   3) said third voltage polarity inverter (318*e*) adapted to receive at said input (316*e*) said gain-adjusted time-dependent fifth bias/collector electrode voltage output (314*c*)
   4) said third voltage polarity inverter (318*e*) adapted to output at said voltage polarity inverter output (320*e*) a polarity-inverted time-dependent fifth bias/collecting electrode voltage (322*e*) by altering the value of time-dependent fifth bias/collector electrode voltage output (309*e*) from negative to positive;
l) said time-dependent voltage aggregator (326) adapted to determine and eliminate the delay time of said polarity-inverted time-dependent third bias/collecting electrode voltage output (322*c*) compared to said polarity-inverted time-dependent first bias/collector electrode voltage output (322*a*) and to generate a time-shifted time-dependent third bias/collecting electrode voltage output;
m) said time-dependent voltage aggregator (326) adapted to determine and eliminate the delay time of said time-dependent fourth bias/collecting electrode voltage output (314*d*) compared to said polarity-inverted time-dependent first bias/collector electrode voltage output (322*a*) and to generate a time-shifted time-dependent fourth bias/collecting electrode voltage output;
n) said time-dependent voltage aggregator (326) adapted to determine and eliminate the delay time of said polarity-inverted time-dependent fifth bias/collecting electrode voltage output (322*d*) compared to said polarity-inverted time-dependent first bias/collector electrode voltage output (322*a*) and to generate a time-shifted time-dependent fifth bias/collecting electrode voltage output;
o) said time-dependent voltage aggregator (326) further adapted determine said time-dependent average output

18 in light of said time-shifted time-dependent third bias/collecting electrode voltage output, said time-shifted gain-adjusted time-dependent fourth bias/collecting electrode voltage output and said time-shifted time-dependent fifth bias/collecting electrode voltage output.

11. A detector system, comprising
a. a detector body (108),
   i. said detector body (108) having a first end (110) and a second end (126),
   ii. said detector body (108) having a discharge section (140) and a reaction section (142),
   iii. said discharge section (140) intermediate said reaction section (142) and said detector body first end (110),
   iv. said reaction section (142) intermediate said discharge section (140) and said detector body second end (110);
b. a first discharge electrode (104) and a second discharge electrode (114) sufficiently distanced for electrical spark generation therebetween;
c. a first bias/collecting electrode (206*a*) having an exposed surface in said reaction section (142)
   i. a first bias source (304*a*) adapted to provide a first bias voltage to said first bias/collecting electrode (206*a*),
   ii. said first bias/collecting electrode (206*a*) adapted to generate a time-dependent first bias/collecting electrode current (305*a*);
d. a second bias/collecting electrode (206*a*) having an exposed surface in said reaction section (142);
   i. a second bias source (304*b*) adapted to provide a second bias voltage to said second bias/collecting electrode (206*b*);
   ii. said second bias/collecting electrode (206*b*) adapted to generate time-dependent second bias/collecting electrode current (305*b*);
e. a first current-to-voltage converter (310*a*) adapted to generate a time-dependent first bias/collector electrode voltage (314*a*) based on said time-dependent first bias/collecting electrode current (305*a*);
f. a second current-to-voltage converter (310*b*) adapted to generate a time-dependent second bias/collector electrode voltage (314*b*) based on said time-dependent second bias/collecting electrode current (305*b*);
g. a first voltage polarity inverter (318*b*) adapted to generate a polarity-inverted time-dependent first bias/collecting electrode voltage (322*b*) by altering the value of time-dependent first bias/collector electrode voltage (314*b*) from negative to positive;
h. a first gain adjuster (311*b*) adapted to generate a gain-adjusted time-dependent second bias/collecting electrode voltage (314*b*) by multiplying said time-dependent second bias/collecting electrode voltage (309*b*) by a first gain value;
i. a time-dependent voltage aggregator (326),
   i. said time-dependent voltage aggregator (326) adapted to receive said polarity-inverted time-dependent first bias/collector electrode voltage (322*a*),
   ii. said time-dependent voltage aggregator (326) adapted to receive said gain-adjusted time-dependent second bias/collector electrode voltage (314*b*),
   iii. said time-dependent voltage aggregator (326) adapted to determine and eliminate the delay time between said polarity-inverted time-dependent first bias/collector electrode voltage output (322*a*) and said gain-adjusted time-dependent second bias/collector electrode voltage output (314*b*) to generate a time-shifted gain-adjusted time-dependent second bias/collector electrode voltage output,
    iv. said time-dependent voltage aggregator (326) adapted to determine a time-dependent average output from said polarity-inverted time-dependent first bias/collector electrode voltage (322) and said time-shifted gain-adjusted time-dependent second bias/collector electrode voltage (314b),
    v. said time-dependent voltage aggregator (326) adapted to output said time dependent average output.

12. A method of analyzing a sample compound comprising the steps of:
  a. providing a detector body (108) having an internal elongated cylindrical cell (138);
  b. providing a first discharge electrode (104) in said detector body (108);
  c. providing a second discharge electrode (116) in said detector body (108) separated from said first discharge electrode (104) sufficient for electrical spark generation;
  d. providing a first bias/collecting electrode (206a) in said detector body (108) in electrical communication with a first bias source (304a) to generate a time-dependent first bias/collecting electrode current (305a) in response to constituents flowing through said detector body (108);
  e. providing a second bias/collecting electrode (206b) in said detector body in electrical communication with a second bias source (304b) to generate a time-dependent first bias/collecting electrode current (305b) in response to constituents flowing through said detector body (108);
  f. generating at a first current-to-voltage converter (307a) a time-dependent first bias/collector electrode voltage (309a) based on said time-dependent first bias/collecting electrode current (305a);
  g. generating at a second current-to-voltage converter (307b) a time-dependent second bias/collector electrode voltage (309b) based on said time-dependent second bias/collecting electrode current (305b);
  h. generating at a voltage polarity inverter (318a) a polarity-inverted time-dependent second bias/collecting electrode voltage (322a) by altering the value of time-dependent first bias/collector electrode voltage (314a) from negative to positive;
  i. applying a gain at a gain adjuster (311b) to said time-dependent second bias/collector electrode voltage (309b) to generate a gain-adjusted time-dependent second bias/collector electrode voltage (314b)
  j. determining and eliminating the delay time between said polarity-inverted time-dependent first bias/collector electrode voltage output (322a) and said gain-adjusted time-dependent second bias/collector electrode voltage output (314b) to generate a time-shifted gain-adjusted time-dependent second bias/collector electrode voltage output,
  k. determining a time-dependent average output from said polarity-inverted time-dependent first bias/collector electrode voltage output (314a) and said time-shifted gain-adjusted time-dependent second bias/collector electrode voltage output, and
  l. displaying said time-dependent average output.

13. A method of analyzing a sample compound comprising the steps of:
  a. providing a detector body (108) having an internal elongated cylindrical cell (138);
  b. providing a first discharge electrode (104) and a second discharge electrode (216) in said detector body (108) separated from said first discharge electrode first end (106) sufficient for electrical spark generation;
  c. transmitting a time-dependent first bias/collecting electrode current (305a) from a first bias/collecting electrode (206a) in said detector body in electrical communication with a first bias source (304a);
  d. transmitting a time-dependent second bias/collecting electrode current (305b) from a second bias/collecting electrode (206b) in said detector body in electrical communication with a second bias source (304b);
  e. passing said time-dependent first bias/collecting electrode current (305a) through a first current-to-voltage converter (307a) and generating a time-dependent first bias/collector electrode voltage (309a);
  f. passing said time-dependent second bias/collecting electrode current (305b) through a second current-to-voltage converter (307b) and generating a time-dependent second bias/collector electrode voltage (309b);
  g. passing said time-dependent first bias/collector electrode voltage (314a) through a voltage polarity inverter (318a) and generating a polarity-inverted time-dependent second bias/collecting electrode voltage (322a) by altering the value from negative to positive;
  h. increasing the gain of said time-dependent second bias/collector electrode voltage (309b) and generating a gain-adjusted time-dependent second bias/collector electrode voltage (314b)
  i. determining and eliminating the delay time between said polarity-inverted time-dependent first bias/collector electrode voltage output (322a) and said gain-adjusted time-dependent second bias/collector electrode voltage output (314b) to generate a time-shifted gain-adjusted time-dependent second bias/collector electrode voltage output,
  j. determining a time-dependent average output from said polarity-inverted time-dependent first bias/collector electrode voltage output (314a) and said time-shifted gain-adjusted time-dependent second bias/collector electrode voltage output, and
  k. displaying said time-dependent average output.

14. A method of analyzing a sample compound comprising the steps of:
  obtaining a plurality of time-dependent outputs, each of said plurality of time-dependent outputs associated with a voltage-biased bias/collecting electrode in the reaction section of a gas detector, each of said plurality of time-dependent outputs having an output strength intensity compared its baseline, said gas detector having a first discharge electrode having a first end, said gas detector having an internal open cylindrical cell;
  eliminating the time delay among said plurality of time-dependent outputs;
  adjusting the intensity of each of said time-dependent outputs by the result of the equation $(R_x^2 \times A_1)/(A_x \times R_1^2)$, where $R_x$ is the distance of said voltage-biased bias/collecting electrode (206a) from said first discharge electrode first end (106) and $A_x$ is the cross-sectional area of the cylindrical cell (138) perpendicular to its centerline (139) at said bias/collecting electrode (206a) and where $R_1$ is the distance of said first bias/collecting electrode (206a) from said first discharge electrode first end (106) and $A_1$ is the cross-sectional area of the cylindrical cell (138) perpendicular to its centerline (139) at said first bias/collecting electrode (206);
  determining an average time-delay eliminated intensity adjusted time-dependent output; and displaying said average time-delay eliminated intensity adjusted time-dependent output.

* * * * *